United States Patent [19]

Nickol

[11] Patent Number: 4,707,189
[45] Date of Patent: Nov. 17, 1987

[54] BIOSTABLE COMPOSITIONS AND THE AQUEOUS SOLUTIONS THEREOF AS THICKENERS FOR AQUEOUS-BASED SYSTEMS

[75] Inventor: Robert G. Nickol, Wilmington, Del.

[73] Assignee: Hercules Incorporated, Wilmington, Del.

[21] Appl. No.: 873,108

[22] Filed: Jun. 10, 1986

Related U.S. Application Data

[63] Continuation of Ser. No. 669,138, Nov. 7, 1984, abandoned.

[51] Int. Cl.$^4$ ............................ C08L 1/08; C08L 1/26; C08L 5/00
[52] U.S. Cl. .................................. 106/176; 106/186; 106/197.2; 106/205; 260/102
[58] Field of Search ............... 106/170, 171, 176, 186, 106/197.2, 181, 205, 208; 260/102; 212/547

[56] References Cited

U.S. PATENT DOCUMENTS

| | | | |
|---|---|---|---|
| 2,514,131 | 7/1950 | Kaszuba | 106/186 |
| 2,694,708 | 11/1954 | Erickson | 252/542 |
| 3,285,959 | 11/1966 | McFarlane | 252/547 |
| 3,455,714 | 7/1969 | Bishop et al. | 106/205 |
| 3,503,895 | 3/1970 | Whelan | 106/181 |
| 3,585,051 | 6/1971 | Matteson | 252/542 |
| 3,666,690 | 5/1972 | Bann | 252/547 |
| 3,681,241 | 8/1972 | Rudy | 252/8.75 |
| 3,951,879 | 4/1976 | Wixon | 252/547 |
| 4,105,461 | 8/1978 | Racciato | 106/205 |
| 4,218,262 | 8/1980 | Warren | 106/208 |
| 4,228,277 | 10/1980 | Landoll | 536/90 |
| 4,238,373 | 12/1980 | Hardy et al. | 252/542 |
| 4,460,766 | 7/1984 | Felcht | 536/98 |
| 4,525,515 | 3/1985 | Peignier | 106/170 |

OTHER PUBLICATIONS

Kirk Othmer, "Encyclopedia of Chemical Technology", Jun. 69, p. 504.
Industrial Gums 2nd Ed., R. L. Whistler, p. 22, 1973.

*Primary Examiner*—Theodore Morris
*Attorney, Agent, or Firm*—Joanne L. Horn; Mark D. Kuller

[57] ABSTRACT

Disclosed is an essentially water-free biostable composition comprising at least one anionic water-soluble polymer containing carboxylate or sulfonate groups and small amounts of at least one cationic quaternary ammonium salt surfactant in a ratio, expressed as moles surfactant divided by mole equivalents of carboxylate or sulfonate groups in the polymer, of from about 0.025 to about 2.0 is provided, which is capable of forming highly viscoelastic solutions when mixed in an aqueous medium. By altering the ratio of cationic surfactant to anionic polymer within the specific ratio range, the viscosity of the aqueous solutions of the composition can be adjusted to a desired level.

The aqueous solutions thereof are useful as thickeners in aqueous-based systems, such as latex paints and shampoos.

18 Claims, No Drawings

BIOSTABLE COMPOSITIONS AND THE AQUEOUS SOLUTIONS THEREOF AS THICKENERS FOR AQUEOUS-BASED SYSTEMS

This application is a continuation of application Ser. No. 669,138, filed Nov. 7, 1984, now abandoned.

This invention relates to an essentially water-free, biostable composition comprising at least one anionic water-soluble polymer and at least one cationic surfactant which composition is capable of being mixed with an aqueous medium to form a highly viscoelastic biostable solution and to separate aqueous solutions of each component of the composition, which when mixed together, give a highly viscoelastic biostable solution of the composition. The essentially water-free biostable composition in concentrated form and the aqueous solutions thereof are useful as thickeners in aqueous-based systems, such as latex paints, and shampoos.

Better thickening efficiency of water-soluble polymers is generally obtained by using higher molecular weight polymers. When the water-soluble polymer is a cellulose ether, a high molecular weight cellulose furnish, such as cotton linters, must be used to prepare the cellulose ether. Typically, such furnishes are much more expensive than wood pulps.

Another method of increasing the viscosity of a water-soluble polymer, particularly an anionic water-soluble polymer, is to crosslink the polymer. Usually, the polymer is crosslinked with polyvalent metal ions. However, not all water-soluble polymers are capable of being crosslinked in this manner. For example, sulfoethylhydroxyethyl cellulose are insensitive to most polyvalent metal ions.

Yet another way to increase the thickening efficiency of water-soluble polymers is to hydrophobically modify the polymer backbone using known methods, such as those described in U.S. Pat. No. 4,228,277. While this works well in terms of enhancing viscosity, it does not allow for adjustments to viscosity at the time of use, since the hydrophobe is attached at the time the polymer is prepared.

High viscosity may also be obtained simply by increasing the concentration of the polymer. Unfortunately, this procedure is frequently inefficient, impractical or both.

Hence, in order to overcome the drawbacks of the present methods of increasing the viscosifying effect of water-soluble polymers, it is desirable to have a water-soluble composition, which has enhanced viscosity in aqueous media, is simple to prepare, and is easy to adjust at the time of use. In addition, it would be beneficial for such water-soluble composition to be available (1) in a concentrated, essentially dry form, (2) in a concentrated highly viscous aqueous solution form, or (3) in separate aqueous solutions of each component of the composition, which have enhanced viscosity when mixed together, all of which are capable of thickening aqueous-based systems.

It is known to and commonly accepted by those skilled in the art that cationic surfactants, when mixed with anionic polymers, cause mutual precipitation. Hence, it was quite unexpected to find that a specific molar ratio of cationic surfactant to anionic polymer exists, which when mixed together in a solution, gives an enhanced viscosifying effect over solutions of the anionic polymer by itself, and do not precipitate out of the solution.

The cationic surfactants alone have little or no ability to viscosify aqueous solutions at conventional thickener concentration levels for the particular aqueous system in question. At extremely high concentration levels, the surfactants would have some viscosifying effect.

According to this invention, an essentially water-free biostable composition comprising at least one anionic water-soluble polymer containing carboxylate or sulfonate groups and small amounts of at least one cationic quaternary ammonium salt surfactant in a ratio, expressed as moles surfactant divided by mole equivalents of carboxylate or sulfide groups in the polymer, of from about 0.025 to about 2.0 is provided, which composition is capable of forming highly viscoelastic solutions when mixed. By altering the ratio of cationic surfactant to anionic polymer within the specific ratio range, the viscosity of the aqueous solutions of the composition can be adjusted to the desired level.

The water-soluble composition can be prepared by mixing at least one dry anionic water-soluble polymer with at least one cationic surfactant in a conventional tumbler until a homogeneous blend of the two dry ingredients is obtained. The dry blend can be dissolved in water to form viscoelastic solutions. Alternatively, separate solutions of at least one anionic water-soluble polymer and of at least one cationic surfactant are prepared, which when admixed form a single solution of enhanced viscosity.

The anionic polymer can be a cellulosic, such as sodium carboxymethylcellulose (CMC), carboxymethylhydroxyethyl cellulose (CMHEC), sulfoethylhydroxyethyl cellulose (SEHEC); natural gums, such as carrageenan, or prepared gums, such as xanthan. Mixtures of the anionic polymers can be used. Typically, the polymer has a molecular weight of 200,000 to 1,000,000, preferably from about 500,000 to about 1,000,000.

Typically the CMC has a degree of substitution (D.S.) from about 0.6 to about 0.9, preferably from about 0.7 to about 0.9.

Suitable carboxymethylhydroxyethyl celluloses include those having a carboxymethyl D.S. from about 0.05 to about 1.5, preferably from about 0.1 to about 1.0, and a hydroxyethyl molar substitution (M.S.) of from about 1.0 to about 3.0, preferably from about 2.0 to about 2.5.

Generally the sulfoethylhydroxyethyl cellulose has a sulfoethyl D.S. of from about 0.05 to about 0.5 and a hydroxyethyl M.S. of from about 1.0 to about 3.0, preferably from about 2.0 to about 2.5.

D.S. is the average number of hydroxyl groups substituted per anhydroglucose unit of the cellulose molecule. M.S. is the average number of moles of ethylene oxide per anhydroglucose unit of the cellulose molecule.

The methods of preparing CMC, carboxymethylhydroxyethyl cellulose and sulfoethylhydroxyethyl cellulose are well known in the art. See, e.g., Whistler, R. L. & BeMiller, J. N., *Industrial Gums,* 649–72, 695–729 (2d Ed. 1973); Pastyr, J. & Pasteka, M., *Cellulose Chem. and Technology,* 389–93 (1978). A variety of CMCs and carboxymethylhydroxyethyl celluloses are available commercially.

The natural or prepared gums are available commercially.

The cationic quaternary ammonium salt surfactant is an essentially water-soluble organic quaternary ammonium salt having at least one long chain alkyl group or rosin moiety and having no more than two long chain alkyl groups or rosin moieties, wherein the long chain alkyl group has at least 8 carbon atoms and is a straight carbon chain or an essentially straight carbon chain. Essentially straight carbon chain as the term is used herein means a carbon chain having a minor amount of branching, i.e., one to two branches having no more than 2 carbon atoms. Preferably, the long chain alkyl group has 12 to 18 carbon atoms and is a straight carbon chain. Most preferably, the long chain alkyl group has 14 to 18 carbon atoms and a straight carbon chain. The quaternary ammonium salts are biocides thereby providing biostability to compositions containing them. Typically the quaternary ammonium salts useful in the practice of this invention have at least one long chain alkyl group of at least ten carbons, preferably at least fifteen carbons, and most preferably at least sixteen carbons. Typical salts include those of the general formula I:

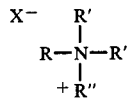

wherein R is $C_{10-22}$ alkyl, R' is H, $C_{1-4}$ alkyl (straight or branched), cycloalkyl having 7 carbon atoms or less, or aralkyl having 8 carbon atoms or less, R'' is H, $C_{8-22}$ alkyl, cycloalkyl having a $C_{8-22}$ alkyl, aralkyl having a $C_{8-22}$ alkyl, or $C_{1-2}$ alkyl substituted aralkyl, the aralkyl having a $C_{8-22}$ alkyl, and X is halogen, acetate, sulfate, methylsulfate or nitrate; of the general formula II:

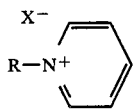

wherein R is $C_{10-22}$ alkyl, and X is halogen, acetate, sulfate, methylsulfate or nitrate; of the general formula III:

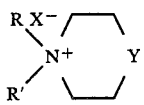

wherein R is $C_{10-22}$ alkyl, R' is H, $CH_3$ or $CH_2CH_3$, Y is $-CH_2$ or O, and X is halogen, acetate, sulfate, methylsulfate or nitrate; of the general formula IV:

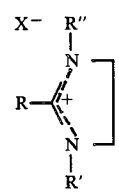

wherein R is $C_{10-22}$ alkyl, R' is $CH_3$, $CH_2CH_3$, or $CH_2CH_2OH$, R'' is H, $CH_3$, $CH_2CH_3$, and X is halogen, acetate, sulfate, methylsulfate or nitrate; of general formula V:

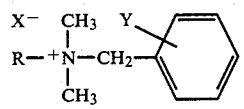

wherein R is $C_{10-22}$ alkyl, Y is H, $CH_3$, $CH_2CH_3$ or halo, and X is halogen, acetate, sulfate, methylsulfate or nitrate; or of the general formula VI:

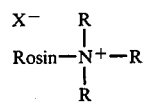

wherein Rosin is abietyl, tetrahydroabietyl or dehydroabietyl, R is H, $CH_3$ or $CH_2CH_3$, and X is halogen, acetate, sulfate, methylsulfate or nitrate.

Typical $C_{10-22}$ alkyl groups are soya, coco, dodecyl, stearyl, myristyl, cetyl, oleyl, tallow and hydrogenated tallow. Suitable $C_{1-4}$ alkyl (straight or branched) groups include methyl, ethyl, propyl and isopropyl; and suitable $C_{1-2}$ alkyl groups include methyl and ethyl. Cyclohexane is a typical cycloalkyl having 7 carbon atoms or less; and tolyl is a typical aralkyl having 8 carbon stoms or less. Suitable halogen atoms include chlorine and bromine.

The molar ratio of surfactant to carboxylate or sulfonate groups of the polymer is determined from the weight ratios of the surfactant and polymer by known methods. First, the equivalent weight of a polymer useful in this invention is determined: (1) take CMHEC for example, the equivalent weight is determined by calculating the molecular weight of an anhydroglucose unit of the cellulose backbone polymer; (2) multiplying the carboxymethyl D.S. by the molecular weight of sodium carboxymethyl group; (3) multiplying the hydroxyethyl M.S. by the molecular weight of the hydroxyethyl group; (4) adding items (1), (2) and (3) to get the grams per anhydroglucose unit of the cellulose molecule and (5) dividing the number of grams per anhydroglucose unit of the cellulose molecule by the carboxymethyl D.S. which gives you the number of grams per equivalent of carboxylate or sulfonate groups for each gram of the polymer. Similarly, the grams per equivalent of sulfonate groups for each group of a polymer having sulfonate groups is determined. The molecular weight (g/mole) of the surfactant is then determined. Hence, a weight ratio of moles surfactant divided by mole equivalents of carboxylate or sulfonate groups of 0.1 would correspond to (0.1 g divided by the g/mole of surfactant) divided by (1 g polymer divided by the g/equivalents of carboxylate or sulfonate groups).

The various examples below are illustrative of this invention. The anionic polymer component, although in particulate form, generally contains a certain amount of moisture. It can contain up to about 11% moisture, by weight, of the component, but typically it contains about 3.0% to about 6.0% moisture.

All parts and percentages are by weight throughout this specification unless otherwise specified.

EXAMPLE 1

This example illustrates an embodiment of the composition this invention and how to prepare it.

A vial is charged with 3.18 g of carboxymethylhydroxyethyl cellulose (CMHEC) (5.7% moisture content), having a carboxymethyl D.S. of 0.4, a hydroxyethyl M.S. of 2.0; and with 0.3 g of cetyltrimethylammonium bromide surfactant. The vial is tumbled for two hours in a conventional tumbler to form a homogeneously blended powder concentrate.

EXAMPLE 2

This example illustrates another embodiment of the composition of this invention and how to prepare it.

A mixing vessel affixed with a stirrer is charged with 198.84 g. of distilled water. Stirring is commenced and 1.16 g of the concentrate of Example 1 is added. Stirring is continued for about two hours, with periodic breaking of lumps, if necessary, until the powder concentrate is dissolved in the water. The solution thus formed contains 0.5% CMHEC and 0.05% surfactant by weight.

The solution is left standing in the vessel at room temperature (23° C.) for 24 hours to overcome the effects of shear in preparing the solution on the viscosity of the solution. The viscosity is then measured with a Brookfield LVF synchro-lectric viscometer at 23° C. at 6 rpm and at 30 rpm using a No. 5 spindle. The viscosity of the solution is 47,400 centipoises (cps) at 6 rpm and 18,880 cps at 30 rpm. The relative viscosity, i.e. the viscosity of the polymer surfactant mixture divided by the viscosity of the pure polymer at the same polymer concentration, shear rate (rpm) and temperature, is 121 cps at 6 rpm and 63.5 at 30 rpm.

CONTROL 1

A vessel affixed with a stirrer is charged with 198.94 g of distilled water. Stirring is commenced and 1.06 g of the CMHEC of Example 1 is added. Stirring is continued for about 2 hours, with periodic breaking of lumps, if necessary, until the CMHEC is dissolved in the water. The solution thus formed contains 0.5% CMHEC by weight. The solution is left standing in the vessel at room temperature (23° C.) for 24 hours to overcome the effects of shear in preparing the solution on the viscosity of the solution. The viscosity is then measured as set forth above in Example 2. The viscosity of this solution is 390 cps at 6 rpm and 296 cps at 30 rpm.

EXAMPLES 3-8

These examples illustrate other embodiments of the composition of this invention.

A powder concentrate of the anionic polymer and cationic surfactant composition is prepared according to the procedure of Example 1 and a solution of the composition is prepared according to the procedure of Example 2. The same surfactant, cetyltrimethylammonium bromide, is used in these examples and the polymer is varied. All viscosity is measured after the solution is left standing for 24 hours with a Brookfield LVF synchro-lectric viscometer at 23° C. at 6 rpm and at 30 rpm. The formulations and relative viscosities thereof together which are set forth in Table I.

TABLE I

| Example | Anionic Polymer | Cationic Surfactant CTAB[a], g | Polymer Conc., % | Water, g | Wt. Ratio Surfactant Polymer, % | Relative Viscosity[b], 6 rpm, cps | Relative Viscosity[b], 30 rpm, cps | Spindle No. |
|---|---|---|---|---|---|---|---|---|
| 3 | CMC 7H having a carboxymethyl D.S. of 0.7 (1.12 g) (10.7% moisture content) | 0.10 | 0.5 | 198.78 | 0.1 | 2.3 | 1.73 | 2 |
| 4 | Xanthan (1.09 g) (8.3% moisture content) | 0.10 | 0.5 | 198.81 | 0.1 | 1.5 | 1.26 | 2 |
| 5 | SEHEC having a sulfoethyl D.S. of 0.5, a hydroxyethyl M.S. of 2.5 (1.03 g) (2.9% moisture content) | 0.10 | 0.5 | 198.87 | 0.1 | 47.5 | 15.8 | 3 |
| 6 | CMHEC 420G having a carboxymethyl D.S. of 0.4, a hydroxyethyl M.S. of 2.0 (2.14 g) (6.5% moisture content) | 0.20 | 1.0 | 197.66 | 0.1 | 5.9 | 6.6 | 1 |
| 7 | CMHEC having a carboxymethyl D.S. of 0.25 a hydroxyethyl M.S. of 2.0 (1.11 g) (9.9% moisture content) | 0.10 | 0.5 | 198.79 | 0.1 | 80.8 | 34.9 | 4 |
| 8 | CMHEC having a carboxymethyl D.S. of 0.1, a hydroxyethyl M.S. of 2.3 (1.05 g) (4.8% moisture content) | 0.10 | 0.5 | 198.85 | 0.1 | 82.4 | 42.6 | 4 |

[a]Cetyltrimethylammonium bromide
[b]Viscosity of aqueous solution of the polymer and surfactant composition divided by the viscosity of the pure polymer at the same concentrations, shear rates (rpm) measured with the same viscometer at 24° C.

The aqueous compositions having the highest relative viscosity, i.e., >100 cps, are the best viscosifiers. However, workers skilled in the art may find compositions imparting lower relative viscosities to be suited to their particular needs. To have a viscosifying effect, however, the aqueous compositions must have a relative viscosity of greater than 1.0. Although the nature of the viscosifying effect is not entirely known, it is theorized that the ability of the anionic polymer and cationic surfactant to form complexes and the molecular weight of the polymer used each play a role.

EXAMPLES 9-14

These examples illustrate other embodiments of this invention.

A powder concentrate of the anionic polymer and cationic surfactant composition is prepared according to the procedure of Example 1 and an aqueous solution according to the procedure of Example 2. The same polymer, namely CMHEC having a carboxymethyl D.S. of 0.4, a hydroxyethyl M.S. of 2.0, is used in these examples and the surfactant is varied. The viscosity is measured after the solution is left standing for 24 hours with a Brookfield LVF synchro-lectric viscometer at 23° C. at 6 rpm and at 30 rpm using an appropriate spindle. The formulations and relative viscosities thereof are set forth in Table II.

TABLE II

| | Cationic Surfactant | CMHEC 420H, g | Polymer Conc., % | Water, g | Wt. Ratio Surfactant Polymer, % | Relative Viscosity[a], 6 rpm, cps | Relative Viscosity[a], 30 rpm, cps | Spindle No. |
|---|---|---|---|---|---|---|---|---|
| Example | | | | | | | | |
| 2 | Cetyltrimethylammonium bromide (0.1 g) | 1.07 | 0.5 | 198.83 | 0.1 | 121.0 | 63.5 | 5 |
| 9 | Dodecyltrimethylammonium bromide (0.1 g) | 1.07 | 0.5 | 198.83 | 0.1 | 1.59 | 1.48 | 2 |
| 10 | Myristyltrimethylammonium bromide (0.1 g) | 1.07 | 0.5 | 198.83 | 0.1 | 23.4 | 16.98 | 4 |
| 11 | Stearyltrimethylammonium chloride (0.2 g) | 2.14 | 1.0 | 197.66 | 0.1 | 139.0 | 62.5 | 4 |
| 12 | Dehydroabietyl ammonium chloride (0.1 g) | 1.07 | 0.5 | 198.83 | 0.1 | 43.5 | 15.0 | 4 |
| 13 | Dehydroabietyl ammonium acetate (0.1 g) | 1.07 | 0.5 | 198.83 | 0.1 | 63.8 | 20.2 | 4 |
| 14 | Cetylpyridinium chloride (0.1 g) | 1.07 | 0.5 | 198.83 | 0.1 | 182.5 | 86.2 | 5 |
| Control | | | | | | | | |
| 1 | Tetrabutylammonium bromide (0.1 g) | 1.07 | 0.5 | 198.83 | 0.1 | 1.0 | 1.0 | 1 |
| 2 | Hexamethylenebis(trimethylammonium bromide) (0.1 g) | 1.07 | 0.5 | 198.83 | 0.1 | 0.86 | 0.91 | 1 |

[a]Viscosity of aqueous solution of the polymer and surfactant composition divided by the viscosity of the pure polymer at the same concentrations, shear rates (rpm) measured with the same viscometer at 24° C.

Distilled water is used in all the examples since salts are known to interfere with ionic interactions. To determine the effect of tap water on the viscosity enhancing effect of aqueous solutions of the compositions of this invention, aqueous solutions of 0.5% of CMHEC (8.0% moisture content) having a carboxymethyl D.S. of 0.4 and a hydroxyethyl M.S. of 2.0 in both distilled and tap water and aqueous solutions of 0.5% of the same CMHEC and 0.05% cetyltrimethylammonium bromide (CTAB) in both distilled and tap water were tested. The results are shown in Table IV.

TABLE IV

| Ingredients | Viscosity,[1] cps at 6 rpm | Viscosity,[1] cps at 30 rpm | Relative[2] Viscosity, cps at 6 rpm | Relative[2] Viscosity, cps at 30 rpm |
|---|---|---|---|---|
| CMHEC in distilled water | 186 | 163 | 1 | 1 |
| CMHEC in tap water | 158 | 146 | 1 | 1 |
| CMHEC and CTAB in distilled water | 28,600 | 24,640 | 154 | 151 |
| CMHEC and CTAB in tap water | 11,600 | 10,000 | 73.4 | 68.5 |

[1]Measured at 23° C. after standing 24 hours with a Brookfield LVT viscosity using spindle 1 for the aqueous solutions of CMHEC alone and spindle 4 for the aqueous solutions of CMHEC and CTAB.
[2]The viscosity divided by the viscosity of a control solution containing only the polymer where the viscosity of the control solution is measured in the same manner as set forth in [1] above.

From the above, it is clear that hard water diminishes, but does not eliminate, the viscosity enhancing effect of the composition. Hence, distilled water is preferred.

The viscoelasticity of the aqueous solutions of the compositions of this invention are measured by oscillatory shear viscometry. The storage modulus, G' (a measure of elasticity), and the loss modulus G" (a measure of the viscous loss of energy) are measured. The supremacy of the G' value over the G" value after the addition of a small amount of a quaternary ammonium salt surfactant indicates the increased viscoelastic character of the solution.

The viscoelastic measurements of Example 2, which is representative, are shown in Table III below:

TABLE III

| | Control 1 | Example 2 |
|---|---|---|
| G', dynes/cm$^2$ | 0.5 | 300 |

TABLE III-continued

| | Control 1 | Example 2 |
|---|---|---|
| G", dynes/CM$^2$ | 2.0 | 100 |

Hence, this invention provides compositions which when mixed with water give solutions having enhanced viscosities. The viscosity of the solution can be adjusted by simply adjusting the amount of surfactant used.

Features, advantages and other specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What is claimed is:

1. An essentially water-free biostable composition consisting essentially of a powder concentrate of at least one anionic water-soluble polymer containing carboxylate or sulfonate groups selected from the group consisting of sodium carboxymethylcellulose, carboxymethylhydroxyethyl cellulose, sulfoethylhydroxyethyl cellulose, prepared gums and natural gums and at least one cationic quaternary ammonium salt surfactant in a ratio, expressed as moles surfactant divided by mole equivalents of carboxylate or sulfonate groups in the polymer, of from about 0.025 to about 2.0, which composition is capable of forming a highly viscoelastic solution when mixed in an aqueous medium.

2. The composition of claim 1 wherein the anionic water-soluble polymer is carrageenan or xanthan.

3. The composition of claim 1 wherein the cationic quaternary ammonium salt surfactant is selected from the group consisting of quaternary ammonium salts having the general formula I:

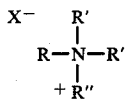

wherein R is $C_{10-22}$ alkyl, R' is H, $C_{1-4}$ alkyl (straight or branched), cycloalkyl having 7 carbon atoms or less, or aralkyl having 8 carbon atoms or less, R" is H, $C_{8-22}$ alkyl, cycloalkyl having a $C_{8-22}$ alkyl, aralkyl having a $C_{8-22}$ alkyl, or $C_{1-2}$ alkyl substituted aralkyl, the aralkyl having a $C_{8-22}$ alkyl, and X is halogen, acetate, sulfate, methylsulfate or nitrate; of the general formula II:

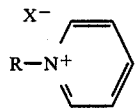

wherein R is $C_{10-22}$ alkyl, and X is halogen, acetate, sulfate, methylsulfate or nitrate; of the general formula III:

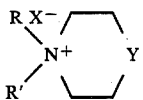

wherein R is $C_{10-22}$ alkyl, R' is H, $CH_3$ or $CH_2CH_3$, Y is $-CH_2$ or O, and X is halogen, acetate, sulfate, methylsulfate or nitrate; of the general formula IV:

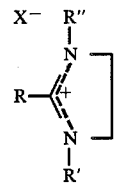

wherein R is $C_{10-22}$ alkyl, R' is $CH_3$, $CH_2CH_3$, or $CH_2CH_2OH$, R" is H, $CH_3$, $CH_2CH_3$, and X is halogen, acetate, sulfate, methylsulfate or nitrate; of general formula V:

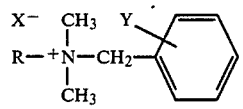

wherein R is $C_{10-22}$ alkyl, Y is H, $CH_3$, $CH_2CH_3$ or halo, and X is halogen, acetate, sulfate, methylsulfate or nitrate; or of the general formula VI:

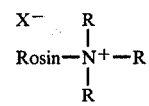

wherein Rosin is abietyl, tetrahydroabietyl or dehydroabietyl, R is H, $CH_3$ or $CH_2CH_3$, and X is halogen, acetate, sulfate, methylsulfate or nitrate.

4. The composition of claim 1 wherein the anionic polymer is a sodium carboxymethylcellulose.

5. The composition of claim 4 wherein the sodium carboxymethylcellulose has a D.S. from about 0.6 to about 0.9.

6. The composition of claim 1 wherein the anionic polymer is a carboxymethylhydroxyethyl cellulose.

7. The composition of claim 6 wherein the carboxymethylhydroxyethyl cellulose has a carboxymethyl D.S. from about 0.05 to about 1.5 and a hydroxyethyl M.S. of from about 1.0 to about 3.0.

8. The composition of claim 3 wherein the cationic quaternary ammonium salt surfactant has the general formula I.

9. The composition of claim 3 wherein the cationic quaternary ammonium salt surfactant has the general formula II.

10. The composition of claim 3 wherein the cationic quaternary ammonium salt surfactant has the general formula III.

11. The composition of claim 3 wherein the cationic quaternary ammonium salt surfactant has the general formula IV.

12. The composition of claim 3 wherein the cationic quaternary ammonium salt surfactant has the general formula V.

13. The composition of claim 3 wherein the cationic quaternary ammonium salt surfactant has the general formula VI.

14. The composition of claim 1 wherein the anionic water-soluble polymer is the sulfoethylhydroxyethyl cellulose.

15. The composition of claim 14 wherein the sulfoethylhydroxyethyl cellulose has a sulfoethyl D.S. from about 0.05 to about 0.5 and a hydroxyethyl M.S. from about 1.0 to about 3.0.

16. The composition of claim 1 wherein the anionic water-soluble polymer has a molecular weight in the range of 200,000 to 1,000,000.

17. The composition of claim 16 wherein the cationic quaternary ammonium salt surfactant has one or two substituents selected from the group consisting of (a) straight long-chain alkyl groups having at least 8 carbon atioms and (b) rosin moieties.

18. The composition as claimed in claim 17 wherein the one or two substituents are straight long-chain alkyl groups containing 12 to 18 carbon atoms and having 0, 1 or 2 branches containing one or two carbon atoms.

* * * * *

UNITED STATES PATENT AND TRADEMARK OFFICE
CERTIFICATE OF CORRECTION

PATENT NO. : 4,707,189
DATED : November 17, 1987
INVENTOR(S) : Robert G. Nickol

It is certified that error appears in the above-identified patent and that said Letters Patent are hereby corrected as shown below:

Columns 7-8 (TABLE II) - Lines 20 & 21

" Hexamethylenebis (trimethylammonium bromide) "

Should read

-- Hexamethylenebis (trimethylammonium) bromide --

Column 10 - Line 63 " atioms and (b) rosin "

Should read -- atoms and (b) rosin --

Signed and Sealed this

Nineteenth Day of April, 1988

Attest:

DONALD J. QUIGG

Attesting Officer        Commissioner of Patents and Trademarks